United States Patent [19]
Stohrer et al.

[11] Patent Number: 5,641,850
[45] Date of Patent: Jun. 24, 1997

[54] PROCESS FOR THE PREPARATION OF LIQUID-CRYSTALLINE POLYORGANOSILOXANES CONTAINING (METH)ACRYLOXY GROUPS

[75] Inventors: Juergen Stohrer, München; Franz-Heinrich Kreuzer, Martinsried; Hans-Joachim Luckas, München, all of Germany

[73] Assignee: Consortium fur electrochemische Industrie GmbH, Munich, Germany

[21] Appl. No.: 555,957

[22] Filed: Nov. 9, 1995

[30] Foreign Application Priority Data

Nov. 10, 1994 [DE] Germany ............... 44 40 209.0

[51] Int. Cl.$^6$ ................................. C08G 77/04
[52] U.S. Cl. ....................... 528/15; 528/25; 528/26; 528/31
[58] Field of Search ............... 528/25, 26, 15

[56] References Cited

U.S. PATENT DOCUMENTS

| | | | |
|---|---|---|---|
| 4,388,453 | 6/1983 | Finkelmann et al. | 528/15 |
| 4,410,570 | 10/1983 | Kreuzer et al. | 427/374.1 |
| 5,211,877 | 5/1993 | Andrejewski et al. | 252/299.01 |

FOREIGN PATENT DOCUMENTS

| | | |
|---|---|---|
| 0562584 | 9/1993 | European Pat. Off. . |
| 3110048 | 9/1982 | Germany . |

*Primary Examiner*—Ralph H. Dean
*Attorney, Agent, or Firm*—Martin Connaughton

[57] ABSTRACT

Liquid-crystalline polyorganosiloxanes containing methacryloxy and/or acryloxy groups are prepared by reaction of polyorganosiloxanes containing hydrogen atoms bonded directly to silicon atoms with alkenes and/or alkynes containing mesogenic groups in two steps, wherein the polyorganosiloxanes mentioned are reacted in a first step with alkene and/or alkyne containing mesogenic groups and are reacted in a second step with an alkene and/or alkyne containing at least one methacryloxy and/or acryloxy group and mesogenic groups.

7 Claims, No Drawings

PROCESS FOR THE PREPARATION OF LIQUID-CRYSTALLINE POLYORGANOSILOXANES CONTAINING (METH)ACRYLOXY GROUPS

FIELD OF THE INVENTION

The present invention relates to the preparation of liquid-crystalline polyorganosiloxanes containing acryloxy and/or methacryloxy groups and to the crosslinking of the liquid-crystalline polyorganosiloxanes.

BACKGROUND OF INVENTION

Methacryloxy and/or acryloxy groups are introduced into liquid-crystalline polyorganosiloxanes so that the latter can be crosslinked. This crosslinking can take place, for example, by a free radical or ionic reaction on the ethylenic double bonds of the (meth)acryloxy groups. In order to obtain highly three-dimensionally crosslinked liquid-crystalline polyorganosiloxane, it is desirable to introduce the highest possible content of (meth)acryloxy groups into the polyorganosiloxane. However, if liquid-crystalline polyorganosiloxanes having a high content of (meth)acryloxy groups are prepared, according to U.S. Pat. No. 4,388,453, only hazy and rough films can be produced with these materials after orientation. The use of the non-mesogenic bifunctional monomers mentioned, such as allyl (meth) acrylate, results in materials having a narrow phase range and very poor orientability. Unreacted monomers without (meth)acryloxy groups which cannot be incorporated into the three-dimensional network and impair the properties of the networks remain in the materials.

If liquid-crystalline polyorganosiloxanes having a high content of (meth)acryloxy groups are prepared by the process described in U.S. Pat. No. 5,211,877, films of improved but still unsatisfactory transparency can be produced with these materials. In addition, the expensive use of protective groups is necessary according to U.S. Pat. No. 5,211,877. Complete removal of excess (meth)acrylic acid and/or derivatives thereof cannot be achieved, or can be achieved only with great additional expenditure, in the process described in U.S. Pat. No. 5,211,877, so that the materials obtained cause an intensive odor nuisance and readily polymerize prematurely.

SUMMARY OF INVENTION

The object of the present invention was to provide a process for the preparation of methacryl- and/or acryloxy-functional liquid-crystalline polyorganosiloxanes and compositions comprising these which are not hazy, even with a high content of (meth)acryloxy groups, and have no noticeable smell, and, without expensive working up, are free from monomers which do not contain (meth)acryl and from acid and/or basic catalysts.

The present invention relates to a process for the preparation of liquid-crystalline polyorganosiloxanes containing methacryloxy and/or acryloxy groups by reaction of polyorganosiloxanes containing hydrogen atoms bonded directly to silicon atoms (H-siloxanes) with alkenes and/or alkynes containing mesogenic groups, the polyorganosiloxanes mentioned being reacted in a first step with alkene and/or alkyne containing mesogenic groups and being reacted in a second step with an alkene and/or alkyne containing at least one methacryloxy and/or acryloxy group and mesogenic groups.

The polyorganosiloxanes mentioned containing hydrogen atoms bonded directly to silicon atoms are preferably those which are built up from at least three of the units of the formula $$[R_pH_qSiO_{(4-p-q)/2}] \quad (I),$$

in which

R is identical or different, $C_1$- to $C_{18}$-hydrocarbon radicals optionally substituted by halogen atoms or cyano groups, p is an integer having a value from 0 to 3 and an average value from 0.8 to 2.2, q is an integer having a value from 0 to 3, with an average value wherein at least one and on average at least two hydrogen atoms bonded directly to silicon atoms are present per molecule, and the sum of p and q is not more than 3.

Examples of unsubstituted radicals R are alkyl radicals, such as the methyl, ethyl, n-propyl, iso-propyl, n-butyl, iso-butyl, tert-butyl, n-pentyl, iso-pentyl, neo-pentyl and tert-pentyl radical, hexyl radicals, such as the n-hexyl radical, heptyl radicals, such as the n-heptyl radical, octyl radicals, such as the n-octyl radical and iso-octyl radicals, such as the 2,2,4-trimethylpentyl radical, nonyl radicals, such as the n-nonyl radical, decyl radicals, such as the n-decyl radical, dodecyl radicals, such as the n-dodecyl radical; and octadecyl radicals, such as the n-octadecyl radical; alkenyl radicals, such as the vinyl and the allyl radical; cycloalkyl radicals, such as cyclopentyl, cyclohexyl and cycloheptyl radicals and methylcyclohexyl radicals; aryl radicals, such as the phenyl, naphthyl and anthryl and phenanthryl radical; alkaryl radicals, such as o-, m- and p-tolyl radicals, xylyl radicals and ethylphenyl radicals; and aralkyl radicals, such as the benzyl radical and the α- and the β-phenylethyl radical.

Examples of substituted radicals R are cyanoalkyl radicals, such as the β-cyanoethyl radical, and halogenated hydrocarbon radicals, for example haloalkyl radicals, such as the 3,3,3-trifluoro-n-propyl radical, the 2,2,2',2',2',2'-hexafluoroisopropyl radical and the heptafluoroisopropyl radical, and haloaryl radicals, such as the o-, m- and p-chlorophenyl radical.

Preferably, R in each case is an optionally halogenated hydrocarbon radical having 1 to 18, in particular 1 to 10, carbon atoms.

More preferred radicals R are $C_1$- to $C_4$-alkyl radicals and phenyl radicals, in particular methyl radicals.

More preferred polyorganosiloxanes of formula (I) are those which are built up to the extent of at least 90% of their units from units of the formulae $$[(CH_3)_2SiO] \quad (II),$$

$$[(CH_3)_2SiO] \quad (III),$$

$$[H(CH_3)_2SiO_{1/2}] \quad (IV),$$

and $$[(CH_3)_3SiO_{1/2}] \quad (V).$$

The polyorganosiloxanes of formula (I) preferably contain 2 to 100 silicon atoms per molecule, in particular 2 to 15 silicon atoms per molecule.

The alkenes which contain mesogenic groups and are employed in the first step contain no methacryloxy and/or acryloxy group in addition to the alkene group, which can be in the form of a methacryloxy and/or acryloxy group. The alkynes containing mesogenic groups employed in the first step contain no methacryloxy and/or acryloxy group.

Alkenes or alkynes which contain mesogenic groups and can be employed are those compounds which have been employed to date for the preparation of liquid-crystalline polyorganosiloxanes by addition of ethylenically or acetylenically unsaturated compounds containing mesogenic groups onto hydrogen atoms, bonded directly to silicon atoms, or organosilanes and polyorganosiloxanes.

The term "mesogenic groups" is well known in the technical field. These are groups which can give rise to liquid-crystalline properties in a molecule. Examples of mesogenic groups are derivatives of cyclohexane, such as cyclohexane-carboxylic acid cyclohexyl esters, cyclohexanecarboxylic acid phenyl esters, cyclohexyl phenyl ethers, cyclohexyl benzenes, dicyclohexyl derivatives, derivatives of stilbene, benzoic acid phenyl ester and its derivatives, steroids, such as cholesterol, and derivatives thereof, such as cholesterol esters, cholestane and derivatives thereof, benzylideneaniline, azobenzene and its derivatives, azoxybenzene and derivatives thereof, alkyl and alkoxy derivatives of biphenyl, and Schiff's bases. For application reasons, it is often desirable for the mesogenic groups to contain polar functions, such as, the nitrile group, in order to achieve a high dielectric anisotropy effect in the liquid crystal.

Alkenes and alkynes which contain mesogenic groups and are employed in the first step are preferably those of the formula $$B\text{-}(X^1{}_a\text{—}A^1{}_b\text{—}A^2{}_c)_d\text{—}Z_e\text{—}(\text{—}X^2{}_f\text{—}A^3{}_g\text{—}A^4{}_h\text{—})_i\text{—}A^5 \quad (VI),$$

in which
B is a monovalent hydrocarbon radical of the formula $C_nH_m$ which is optionally substituted by halogen atoms and in which one or more non-adjacent methylene units can be replaced by oxygen atoms,
n is an integer having a value from 2 to 20,
m is an integer having the value (2n−1) or (2n−3),
$X^1$ and $X^2$ are identical or different divalent radicals from the group consisting of —O—, —COO—, —CONH—, —CO—, —S—, —C≡C—, —CH=CH—, —CH$_2$—CH$_2$—, —CH=N, —N=N— and —N=N(O)—,
$A^1$, $A^2$, $A^3$ and $A^4$ are identical or different divalent radicals, selected from the group consisting of 1,4-phenylene or 1,4-cyclohexylene radicals, substituted arylenes having 6 to 18 carbon atoms, substituted cycloalkylenes having 6 to 18 carbon atoms and heteroarylene having 4 to 10 carbon atoms,
Z is identical or different di- to tetravalent benzene, 1,4-cyclohexane or 1,3-cyclopentane radicals,
$A^5$ is identical or different, saturated or olefinically unsaturated alkyl, alkoxy or cycloalkyl radicals, having 1 to 16 carbon atoms, steroid radicals, halogen atoms, hydrogen atoms, hydroxyl, nitrile and trialkylsiloxy groups, having alkyl radicals which have 1 to 8 carbon atoms,
a, b, c, d, f, g, h, and i independently of one another are identical or different integers having a value of 0, 1, 2 or 3, and sum of a+b+c+d+e+f+g+h+i is at least 2 and the sum of d and i is not more than 4, and
e is a number having the value 0 or 1.

Examples of radicals $A^5$ are the examples given above for R for alkyl radicals, alkenyl radicals and cycloalkyl radicals; alkyloxy radicals, such as the methoxy, ethoxy, n-propoxy, iso-propoxy, n-, sec- and tert-butoxy radicals, pentoxy, hexoxy, octoxy, decoxy and hexadecoxy radicals; alkenoxy radicals, such as the allyloxy radical and butenyloxy, pentenyloxy, hexenyloxy, octenyloxy, decenyloxy and hexadecenyloxy radicals; cycloalkenyl radicals, such as cyclopentenyl, cyclohexenyl and cycloheptenyl radicals; steroid radicals, such as the cholestane, cholesteryl and doristeryl radical; fluorine, chlorine or bromine atoms; hydrogen atoms; and hydroxyl, nitrile, trimethylsilyloxy, triethylsilyloxy, trimethylsilyl and triethylsilyl groups.

It is more preferable for B—$(X^1{}_a$—$A^1{}_b$—$A^2{}_c)_d$— in formula (VI) to be a radical of the formula

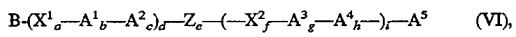

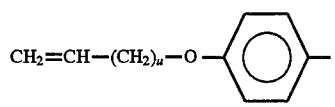

in which u is an integer having a value from 0 to 8, in particular the values 0, 1 or 2.

More preferred compounds of formula (VI) are those the the formula

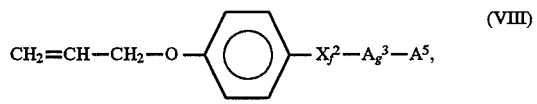

in which $X^2$, $A^3$, $A^5$, f and g have the meanings given above for formula (VI) and, preferably, f has the value 1 and g is either 0 or 1.

Alkenes and alkynes which contain a methacryloxy or acryloxy group and mesogenic groups and are employed in the second step are preferably those of the formula

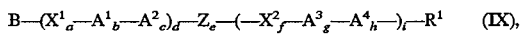

in which
B, $X^1$, $X^2$, Z, $A^1$, $A^2$, $A^3$, $A^4$, a, b, c, d, e, f, g, h and i have the meanings given for formula (VI) and $R^1$ is a radical of the formula

in which
Q is a methyl group or a hydrogen atom and
t is an integer having a value from 0 to 10, and one or more non-adjacent methylene units can be replaced by oxygen atoms.

More preferred radicals $R^1$ are the (meth)acryloxy, (meth)acryloxyethylenoxy, (meth)acryloxydi(ethylenoxy) and (meth)acryloxytri(ethylenoxy) group.

Especially preferred alkenes and alkynes which contain a methacryloxy or acryloxy group and mesogenic groups and are employed in the second step are those of the formula

in which
$R^1$ has the meaning given above in formula (X), in which
t is an integer having the value 0 or 2 and
Q is a methyl group,
$R^2$ is a divalent radical of the formula

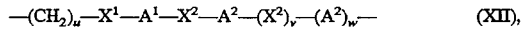

in which
u is an integer having a value from 1 to 8,
v and w have the value 0 or 1 and
$A^1$, $A^2$, $A^3$, $X^1$ and $X^2$ have the meanings given above for formula (VI).

1,4-Phenylene radicals are the preferred meaning for $A^1$, $A^2$ and $A^3$ and the radical —COO— is the preferred meaning for $X^2$.

In all the above formulae, the radicals $X^1$ and $X^2$, if they are not symmetric in structure, can be bonded to any of their bonding partners with each of their ends. Thus, for example, the radical —COO— can also be bonded as —OOC—, the radical —CONH— can also be bonded as —NHCO—, and —CH=N— can also be bonded as —N=CH—.

In all the above formulae, preferred substituents for the substituted arylene and cycloalkylenes $A^1$, $A^2$, $A^3$ and $A^4$ are halogen atoms, $C_1$- to $C_4$-alkoxy radicals, nitro and cyano groups, $C_1$- to $C_6$-alkyl radicals, carboxy($C_1$- to $C_4$-alkyl) radicals and tri-($C_1$- to $C_4$-alkyl)-siloxy radicals.

Preferably, n in above formulae (VI) and (IX) has values from 3 to 10 and m has the value (2n−1).

In all the above formulae, a and f independently of one another preferably have the values 0 or 1.

The reaction according to the invention of the alkenes and alkynes containing mesogenic groups and employed both in the first step and in the second step with the polyorganosiloxanes is preferably carried out in the presence of a catalyst comprising platinum metals and/or compounds thereof. Preferred platinum metals and/or compounds thereof are platinum and/or compounds thereof. All the catalysts which have been employed to date for addition of hydrogen atoms bonded directly to Si atoms onto aliphatically unsaturated compounds can be employed. Examples of such catalysts are metallic and freely divided platinum, which can be on supports, such as silicon dioxide, aluminum oxide or active charcoal, and compounds or complexes of platinum, such as platinum halides, for example $PtCl_4$, $H_2PtCl_6 \cdot 6H_2O$, $Na_2PtCl_4 \cdot 4H_2O$, platinum-olefin complexes, platinum-alcohol complexes, platinum-alcoholate complexes, platinum-ether complexes, platinum-aldehyde complexes, platinum-ketone complexes, including reaction products of $H_2PtCl_6 \cdot 6H_2O$ and cyclohexanone, platinum-vinylsiloxane complexes, in particular platinum-divinyltetramethyldisiloxane complexes with or without a content of detectable inorganically bonded halogen, bis-(gamma-picoline)-platinum dichloride, trimethylenedipyridine-platinum dichloride, dicyclopentadieneplatinum dichloride, dimethylsulfoxideethyleneplatinum (II) dichloride and reaction products of platinum tetrachloride with olefin and primary amine or secondary amine or primary and secondary amine, such as the reaction product of platinum tetrachloride, dissolved in 1-octene, with sec-butylamine, or ammonium-platinum complexes.

The platinum catalyst is preferably employed in amounts of 0.5 to 500 ppm by weight (parts by weight per million parts by weight), in particular 2 to 400 ppm by weight, calculated as elemental platinum and based on the total weight of the H-siloxanes present in the reaction mixture.

During the second step of the reaction according to the invention, oxygen, in particular air is preferably passed through the reaction mixture at a rate of 0.01 to 10, preferably 0.5 to 2 l/min·kg. The two steps of the reaction according to the invention can be carried out under identical reaction conditions, but also under different reaction conditions.

The reaction according to the invention (called hydrosilylation below) can be carried out in the absence or in the presence of solvents, the presence of solvents being preferred. If solvents are used, solvents or solvent mixtures which are largely inert under the reaction conditions, and in particular those having a boiling point or boiling range of up to 120° C. at 0.1 MPa, are preferred. Examples of such solvents are ethers, such as dioxane, tetrahydrofuran, diethyl ether and diethylene glycol dimethyl ether; chlorinated hydrocarbons, such as methylene chloride, chloroform, carbon tetrachloride, 1,2-dichloroethane and trichloroethylene; hydrocarbons, such as pentane, n-hexane, hexane isomer mixtures, heptane, octane, wash benzine, petroleum ether, benzene, toluene or xylenes; ketones, such as acetone, methyl ethyl ketone or methyl isobutyl ketone; carbon disulfide and nitrobenzene, or mixtures of these solvents.

The term solvent does not mean that all the reaction components have to dissolve in this. The reaction can also be carried out in a suspension or emulsion of one or more reaction components. The reaction can also be carried out in a solvent mixture having a miscibility gap, at least one reaction component being soluble in each of the mixed phases.

The hydrosilylation can be carried out under the pressure of the surrounding atmosphere, of about 0.1 MPa (absolute), and it can also be carried out under higher or under lower pressures. Pressures from 0.01 MPa to 1.0 MPa, (absolute) in particular from 0.09 MPa to 0.11 MPa (absolute) are preferred.

The hydrosilylation is preferably carried out at temperatures from 0° C. to 150° C., in particular from 60° C. to 100° C.

In the first step, 0.01 to 0.98 mole, in particular 0.02 to 0.9 mole, of alkene and/or alkyne containing mesogenic groups per gram atom of hydrogen atoms bonded directly to silicon atoms are preferably employed in the hydrosilylation.

The product of the hydrosilylation in the first step does not have to be, and is preferably not, isolated from the reaction mixture. The subsequent second hydrosilylation step is preferably carried out in the same reaction vessel as the first step of hydrosilylation (one-pot reaction).

In the second hydrosilylation step, 0.01 to 5 mole, in particular 0.1 to 2 mole, of alkene and/or alkyne containing methacryloxy and/or acryloxy groups and mesogenic groups per gram atom of hydrogen atoms bonded directly to silicon atoms are preferably employed.

The present invention also relates to liquid-crystalline polyorganosiloxanes containing methacryloxy and/or acryloxy groups which can be prepared by the process according to the invention.

All the reaction components, catalysts, solvents, photoinitiators, UV light sources and the like mentioned above or below can be employed individually or as a mixture. It is possible, for example, for one compound of formulae (I), (VI) and (IX), one platinum catalyst, one solvent and the like to be employed, and it is also possible for mixtures or combinations of the above mentioned substances and apparatuses to be employed.

The liquid-crystalline polyorganosiloxanes containing methacryloxy and/or acryloxy groups which can be prepared by the process according to the invention described above can be polymerized to three-dimensionally crosslinked liquid-crystalline polyorganosiloxanes.

The crosslinking can also be carried out in the presence of other polymerizable compounds. Such polymerizable compounds preferably contain at least two methacryloxy and/or acryloxy groups per molecule.

This crosslinking is preferably effected by means of free radicals which are generated by peroxides, by UV light or by higher-energy electromagnetic radiation other than UV light, or by means of heat. However, the cross-linking can also be effected by means of crosslinking agents containing hydrogen atoms bonded directly to silicon atoms, under catalysis by the above mentioned platinum metal catalysts. It can also be carried out cationically or anionically. Crosslinking by UV light is more preferred.

UV light in this context is to be understood as meaning electromagnetic radiation having a wavelength of 13 nm to 400 nm, in particular 100 nm to 400 nm. Crosslinking by UV light in this case is to be understood as meaning crosslinking with the aid of a radiation source which has a higher intensity of UV light than normal sunlight on the ground. Preferred UV radiation sources are those having an intensity maximum in the range from 200 nm to 400 nm. Such UV lamps are commercially obtainable.

The liquid-crystalline polyorganosiloxanes which can be prepared according to the invention are preferably crosslinked by UV light in the presence of photoinitiators and/or photosensitizers.

Suitable photoinitiators and photosensitizers are optionally substituted acetophenones, propiophenones, benzophenones, anthraquinones, benzils, carbazoles, xanthones, thioxanthones, fluorenes, fluorenones, benzions, naphthalenesulfonic acids and benzaldehydes and cinnamic acids.

Examples of these are fluorenone, fluorene and carbazole; acetophenone; substituted acetophenones, such as 3-methylacetophenone, 2,2'-dimethoxy-2-phenylacetophenone, 4-methylacetophenone, 3-bromoacetophenone, 4-allylacetophenone, p-diacetylbenzene and p-tert-butyltrichloroacetophenone; propiophenone; substituted propiophenones, such as 1-(4-(methylthio)phenyl)-2-morpholino-1-propanone, benzophenone; substituted benzophenones, such as Michler's ketone, 3-methoxybenzophenone, 4,4'-dimethylaminobenzophenone, 4-methylbenzophenone, 4-chlorobenzophenone, 4,4'-dimethoxybenzophenone and 4-chloro-4'-benzylbenzophenone; xanthone; substituted xanthones, such as 3-chloroxanthone, 3,9-dichloroxanthone and 3-chloro-8-nonylxanthone; thioxanthone; substituted thioxanthones, such as isopropenylthioxanthone; anthraquinone; substituted anthraquinones, such as chloroanthraquinone and anthraquinone-1,5-disulfonic acid disodium salt; benzoin; substituted benzoins, such as benzoin methyl ether; benzil; 2-naphthalenesulfonyl chloride; benzaldehyde; and cinnamic acid.

Photoinitiators and/or photosensitizers are preferably employed in the crosslinkable compositions in amounts of 0.01% to 10% by weight, in particular 0.5% to 5% by weight, based on the weight of the liquid-crystalline organopolysiloxane.

It is preferable to add to the crosslinkable compositions polymerization inhibitors, and in particular from 1 ppm to 5000 ppm, especially from 100 to 1000 ppm, based on the total weight of the composition.

Preferred polymerization inhibitors are dihydroxybenzenes, which are optionally subsituted on the ring or etherified on one or both hydroxyl groups by $C_1$- to $C_6$-alkyl groups. Examples of such polymerization inhibitors are hydroquinone, p-methoxyphenol and p-tert-butylpyrocatechol and quinone derivatives. Nitroso compounds are also active as polymerization inhibitors.

The crosslinkable compositions can comprise fillers, pigments, plasticizers, adhesion promotors, other polymers, solvents, emulsifiers, rust-proofing agents proofing agents, stabilizers and other, usually customary additivities.

The crosslinkable compositions are preferably crosslinked by applying them to a substrate at temperatures from −20° C. to +180° C., in particular at +20° C. to +100° C., and orienting them by customary methods, for example by melt application by means of a doctor blade or by electrical or magnetic fields, and subsequently exposing them to radiation from a UV lamp.

The three-dimensionally crosslinked liquid-crystalline polyorganosiloxanes which can be prepared in this manner can be used for the production of membranes for separation of mixtures of substances (for example of gases, such as oxygen and nitrogen) and for controlled release of active compounds (for example of medicaments and agricultural chemicals), in the optical display of electromagnetic fields (optoelectronics), in the field of information storage, of electrographic processes and of light modulation, as a constituent of polarization films, optical filters and reflectors, in coatings, and as coating pigments and stationary phases for gas and liquid chromatography.

They are particularly suitable for coating fares, fabrics, leather, ceramic, wood, metal or plastics for decorative purposes.

In the examples described below, unless stated otherwise,
a) all the amounts data are based on the weight,
b) all the pressures are 0.10 MPa (absolute) and
c) all the temperatures are 20° C.

EXAMPLE 1

Polyorganosiloxane with a (meth)acrylic side chain
a) A solution of 136.8 g of 4-(prop-2-en-1-oxy)benzoic acid cholesterol ester (obtainable in accordance with DE-A 3110048) and 33.0 g of tetramethylcyclotetrasiloxane in 300 ml of toluene was boiled under reflux in the presence of 24 mg of dicyclopentadieneplatinum dichloride for 1 hour. After the solution had cooled to 40° C., a stream of dried air was passed into the solution at 20 ml/min, and a solution of 77.5 g of 4-(prop-2-en-1-oxy)benzoic acid 4-methacryloxyphenyl ester and 150 mg of Q1301 (aluminum-cupferron complex, obtainable from Wako Pure Chemicals, 4040 Neuss) in 300 ml of ethyl acetate was added. The combined solutions were stirred at 70° C. for 30 minutes and then filtered and, after the ethyl acetate had been distilled off, the residue was precipitated twice from toluene/petroleum ether. The physical and thermodynamic data are summarized in Table 1. Evaluation by NMR spectroscopy shows that more than 80% of the 4-(prop-2-en-1-oxy)benzoic acid 4-methacryloxyphenyl ester employed has added on in unchanged form.

b) A solution of 11.55 g of 4-(prop-2-en-1-oxy)benzoic acid 4-phenylphenyl ester and 3.3 g of pentamethylcyclopentasiloxane in 400 ml of toluene was boiled under reflux in the presence of 5 mg of dicyclopentadieneplatinumdichloride for 1 hour. After the solution had cooled to 40° C., a stream of dried air was passed into the solution at 5 ml/min and a solution of 4.65 g of 4-(prop-2-en-1-oxy)benzoic acid 4-methacryloxyphenyl ester and 5 mg of Q1301 in 50 ml of ethyl acetate was added. The combined solutions were stirred at 70° C. for 60 minutes and then filtered and, after the ethyl acetate had been distilled off, the residue was precipitated twice from toluene/petroleum ether. The physical and thermodynamic data are summarized in Table 1.

c) A solution of 3.61 g of 4-(prop-2-en-1-oxy)benzoic acid cholesterol ester and 24.0 g of pentamethyltrisiloxane in 10 ml of xylene was boiled under reflux in the presence of 3 mg of platinum-divinyldisiloxane complex for 1 hour. After the volatile constituents had been distilled off, the residue was cooled to 40° C., a solution of 4.09 g of 4-(prop-2-en-1-oxy)benzoic acid 4-methacryloxyphenyl ester and 5 mg of Q1301 in 40 ml of ethyl acetate was added and a stream of dried air was passed in at 5 ml/min. The combined solutions were stirred at 70° C. for 2 hours and then filtered and, after the ethyl acetate had been distilled off, the residue was precipitated twice from toluene/petroleum ether. The physical and thermodynamic data are summarized in Table 1.

d) A solution of 6.84 g of 4-(prop-2-en-1-oxy)benzoic acid cholesterol ester and 3.3 g of pentamethylcyclopentasiloxane in 100 ml of toluene was boiled under reflux in the presence of 4 mg of dicyclopentadieneplatinum dichloride for 1 hour. After the solution had cooled to 40° C., a stream of dried air was passed into the solution at 5 ml/min and a solution of 11.63 g of 4-(prop-2-en-1-oxy) benzoic acid 4-methacryloxyphenyl ester and 10 mg of Q1301 (obtainable from Wako Pure Chemicals) in 50 ml of ethyl acetate was added. The combined solutions were stirred at 70° C. for 30 minutes and then filtered and, after the ethyl acetate had been distilled off, the residue was precipitated twice from toluene/petroleum ether. The physical and thermodynamic data are summarized in Table 1.

e) A solution of 20.51 g of 4-(prop-2-en-1-oxy)benzoic acid cholesterol ester and 3.3 g of pentamethylcyclopentasiloxane in 100 ml of toluene was boiled under reflux in the presence of 4 mg of dicyclopentadieneplatinum dichloride for 1 hour. After the solution had cooled to 40° C., a stream of dried air was passed into the solution at 5 ml/min and a solution of 3.87 g of 4-(prop-2-en-1-oxy) benzoic acid 4-methacryloxyphenyl ester and 20 mg of Q1301 (obtainable from Wako Pure Chemicals) in 50 ml of ethyl acetate was added. The combined solutions were stirred at 70° C. for 30 minutes and then filtered and, after the ethyl acetate had been distilled off, the residue was precipitated twice from toluene/petroleum ether. The physical and thermodynamic data are summarized in Table 1.

A solution of 13.68 g of 4-(prop-2-en-1-oxy)benzoic acid cholesterol ester and 3.3 g of pentamethylcyclopentasiloxane in 100 ml of toluene was boiled under reflux in the presence of 4 mg of dicyclopentadieneplatinum dichloride for 1 hour. After the solution had cooled to 40° C., a stream of dried air was passed into the solution at 5 ml/min and a solution of 7.85 g of 4-(but-3-enyl)benzoic acid 4-methacryloxyphenyl ester and 20 mg of Q1301 (obtainable from Wako Pure Chemicals) in 50 ml of ethyl acetate was added. The combined solutions were stirred at 70° C. for 30 minutes and then filtered and, after the ethyl acetate had been distilled off, the residue was precipitated twice from toluene/petroleum ether. The physical and thermodynamic data are summarized in Table 1.

g) A solution of 8.45 g of 4-(prop-2-en-1-oxy)benozic acid 4-chlorophenyl ester and 3.82 g of pentamethylcyclopentasiloxane in 100 ml of toluene was boiled under reflux in the presence of 4 mg of dicyclopentadieneplatinum dichloride for 1 hour. After the solution had cooled to 40° C., a stream of dried air was passed into the solution at 5 ml/min and a solution of 9.91 g of 4-(prop-2-en-1-oxy) benzoic acid 4-methacryloxyphenyl ester and 20 mg of Q1301 (obtainable from Wako Pure Chemicals) in 50 ml of ethyl acetate was added. The combined solutions were stirred at 70° C. for 30 minutes and the filtered and, after the ethyl acetate had been distilled off, the residue was precipitated twice from toluene/petroleum ether. The physical and thermodynamic data are summarized in Table 1.

h) A solution of 9.57 g of 4-(prop-2-en-1-oxy)benzoic acid cholesterol ester and 3.3 g of pentamethylcyclopentasiloxane in 100 ml of toluene was boiled under reflux in the presence of 4 mg of dicyclopentadieneplatinum dichloride for 1 hour. After the solution had cooled to 40° C., a stream of dried air was passed into the solution at 5 ml/min and a solution of 12.74 g of 4-(prop-2-en-1-oxy) benzoic acid 4-(4-methacryloxybiphenyl) ester and 20 mg of Q1301 (obtainable from Wako Pure Chemicals) in 50 ml of ethyl acetate was added. The combined solutions were stirred at 70° C. for 30 minutes and then filtered and, after the ethyl acetate had been distilled off, the residue was precipitated twice from toluene/petroleum ether. The physical and thermodynamic data are summarized in Table 1.

Monomers used in Example 1

4-(Prop-2-en-1-oxy)benzoic acid cholesterol ester 4-(Prop-2-en-1-oxy)benzoic acid 4-chlorophenyl ester

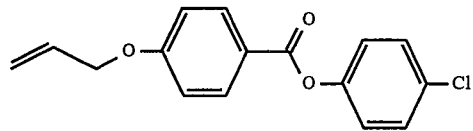

4-(Prop-2-en-1-oxy)benzoic acid 4-methacryloxyphenyl ester

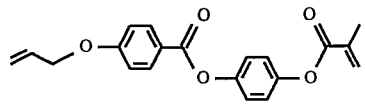

4-(But-3-enyl)benzoic acid 4-methacryloxyphenyl ester

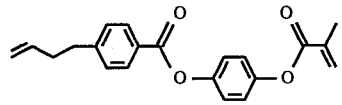

4-(Prop-2-en-1-oxy)benzoic acid 4-(4-methaeryloxybiphenyl)ester

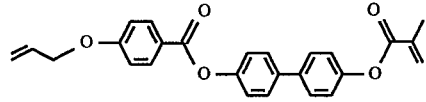

Notes referring to Tables 1 to 3:
1) The content of methacrylic groups indicates the number of methacrylic groups per 100 mesogenic side groups. The value "methacrylic content calculated" corresponds to the assumption that all the methacrylic containing mesogenic monomers employed are bonded to the organo-H-siloxane and and the methacrylic groups are obtained after the hydrosilylation. The value "methacrylic content measured" corresponds to the number of methacrylic groups measured using $^1$H-NMR spectra based on all the mesogenic side chains.
2) determined by measurement of the transmission at 800 nm
3) +++ very strong, ++ strong, + present, 0 not present, determined on a non-reprecipitated sample

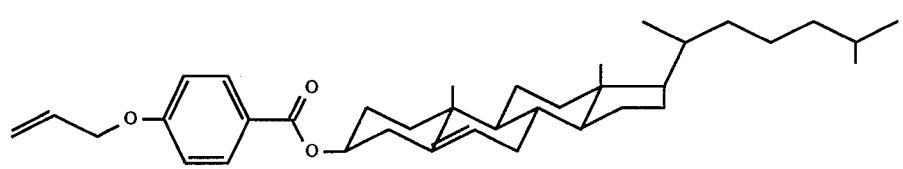

4) determined with the aid of $^1$H-NMR spectra
5) determined with the addition of 500 ppm of Q1301

TABLE 1

| | Example | | | | | | | |
|---|---|---|---|---|---|---|---|---|
| | 1a | 1b | 1c | 1d | 1e | 1f | 1g | 1h |
| Organo-H-siloxane | (MeHSiO)$_5$ | (MeHSiO)$_5$ | Me(MeHSiO)$_3$Me | (MeHSiO)$_5$ | (MeHSiO)$_5$ | (MeHSiO)$_5$ | (MeHSiO)$_5$ | (MeHSiO)$_5$ |
| Methacrylic content calculated (mole %)[1] | 50 | 30 | 33 | 75 | 25 | 50 | 50 | 65 |
| Methacrylic content measured (mole %) | 45 | 28 | 30 | 70 | 22 | 45 | 45 | 52 |
| Haze (%)[2] | 0 | 0 | 0 | 0 | 0 | 0 | 0 | 0 |
| Reflection maximum (nm) | 565 | — | 720 | 650 | 750 | 565 | — | 680 |
| Half-value width (nm) | 80 | — | 85 | 95 | 105 | 80 | — | 85 |
| Glass transition temperature (°C.) | 24 | 35 | 12 | 5 | 50 | 30 | 15 | 38 |
| Clearing point (°C.) | 185 | 155 | 95 | 125 | 195 | 127 | 92 | 167 |
| Smell at 20° C.[3] | 0 | 0 | 0 | 0 | 0 | 0 | 0 | 0 |
| Residual content of first monomer[4] | 0 | 0 | 0 | 0 | 0 | 0 | 0 | 0 |

Comparison Example 2

Polyorganosiloxane with a (meth)acrylic side chain according to U.S. Pat. No. 5,211,877 a) A solution of 13.68 g of 4-(prop-2-en-1-oxy)benzoic acid cholesterol ester, 8.55 g of 4-(prop-2-en-1-oxy)benzoic acid 4-trimethylsilyloxyphenyl ester and 3.30 g of pentamethylcyclopentasiloxane in 100 ml of toluene was boiled under reflux in the presence of 4 mg of dicyclopentadieneplatinum dichloride for 1 hour and, after addition of 10 ml of ethanol and one drop of hydrochloric acid, for an additional 30 minutes. The reaction mixture was concentrated to ⅓ of its original volume, 9.0 g of methacrylic anhydride, 0.4 g of triethylamine and 10 mg of Q1301 were added and the mixture was heated at 100° C. for 1 hour. Volatile constituents were then distilled off and the dark black residue was precipitated twice from toluene in methanol. The physical and thermodynamic data are summarized in Table 2.

b) A solution of 1.65 g of 4-(prop-2-en-1-oxy)benzoic acid 4-biphenyl ester, 5.13 g of 4-(prop-2-en-1-oxy)benzoic acid 4-trimethylsilyloxyphenyl ester and 1.32 g of pentamethylcyclopentasiloxane in 50 ml of toluene was boiled under reflux in the presence of 4 mg of dicyclopentadieneplatinum dichloride for 1 hour and, after addition of 5 ml of ethanol and one drop of hydrochloric acid, for an additional 30 minutes. The reaction mixture was concentrated to ⅓ of its original volume, 10.0 g of methacrylic anhydride, 0.4 g triethylamine and 5 mg of Q1301 were added and the mixture was heated at 100° C. for 1 hour. Volatile constituents were then distilled off and the deep brown residue was precipitated twice from toluene in methanol. The physical and thermodynamic data are summarized in Table 2.

TABLE 2

| | Example | | |
|---|---|---|---|
| | 2a | 2a not precipitated | 2b |
| Organo-H-siloxane | (MeHSiO)$_5$ | (MeHSiO)$_5$ | MeHSiO)$_5$ |
| Crosslinkable side chain (mole %)[1] | 50 | 50 | 75 |
| Methacrylic content (mole %)[1] | 41 | 42 | 61 |
| | 3 | 5 | 3 |
| Haze (%)[2] | | | |
| Reflection maximum (nm) | 520 | 510 | — |
| Half-value width (nm) | 85 | 85 | — |
| Glass transition temperature (°C.)[5] | 47 | 21 | 18 |
| Clearing point (°C.)[5] | 191 | 155 | 105 |
| Smell at 20° C.[3] | + | +++ | + |
| Residual content of first monomer[4] | 0.6 | 1.1 | 0.2 |

Comparison Example 3

Polyorganosiloxane with a (meth)acrylic side chain according to U.S. Pat. No. 4,388,453

A solution of 136.8 g of 4-(prop-2-en-1-oxy)benzoic acid cholesterol ester and 33.0 g of pentamethylcyclopentasiloxane in 300 ml of toluene and of 77.5 g of prop-2-en-1-oxymethacrylic acid allyl alcohol ester and 150 mg of Q1301 (aluminum-cupferron complex, obtainable from Wako Pure Chemicals, 4040 Neuss) in 300 ml of toluene was kept at 70° C. in the presence of 24 mg of dicyclopentadiene-platinum dichloride for 1 hour. After cooling, the product was precipitated from the concentrated solution with methanol. The physical and thermodynamic data are summarized in Table 1. Evaluation by NMR spectroscopy shows that less than 50% of the prop-2-en-1-oxymethacrylic acid allyl alcohol ester has added on in unchanged form. The physical and thermodynamic data are summarized in Table 3.

TABLE 3

| | Example 3 |
|---|---|
| Organo-H-silane | (MeHSiO)$_5$ |
| Crosslinkable side chain (mole %)[1] | 50 |
| Methacryl content (%)[1] | 33 |
| Haze (%)[2] | 3 |

TABLE 3-continued

| | Example 3 |
|---|---|
| Reflection maximum (nm) | 480 |
| Half-value width (nm) | 155 |
| Glass transition temperature (°C.)[5] | 15 |
| Clearing point (°C.)[5] | 89 |
| Odor at 20° C.[3] | 0 |
| Residual content of first monomer[4] | 1.0 |

What is claimed is:

1. A process for the preparation of a liquid-crystalline polyorganosiloxane containing methacryloxy and/or acryloxy groups by reaction of a polyorganosiloxane containing hydrogen atoms bonded directly to silicon atoms with alkenes and/or alkynes containing mesogenic groups, wherein the polyorganosiloxane is reacted in a first step with an alkene and/or alkyne containing mesogenic groups and is reacted in a second step with an alkene and/or alkyne containing at least one methacryloxy and/or acryloxy group and mesogenic groups.

2. The process as claimed in claim 1, wherein the polyorganosiloxane containing hydrogen atoms bonded directly to the silicon atom is one comprising at least three units of the formula $$[R_pH_qSiO_{(4-p-q)/2}] \quad (I),$$

wherein

R is identical or different, $C_1$- to $C_{18}$-hydrocarbon radicals optionally substituted by halogen atoms or cyano groups, p is an integer having a value from 0 to 3 and an average value from 0.8 to 2.2, q is an integer having a value from 0 to 3, with an average value of at least one and on average at least two hydrogen atoms bonded directly to silicon atoms are present per molecule, and the sum of p and q is not more than 3.

3. The process as claimed in claim 1, wherein the alkene and/or alkyne containing mesogenic groups of the first step is one of the formula

in which

B is a monovalent hydrocarbon radical of the formula $C_nH_m$ which is optionally substituted by halogen atoms and in which one or more non-adjacent methylene units can be replaced by oxygen atoms, n is an integer having a value from 2 to 20, m is an integer having the value (2n−1) or (2n−3), $X^1$ and $X^2$ are identical or different divalent radicals from the group consisting of —O—, —COO—, —CONH—, —CO—, —S—, —C≡C—, —CH=CH—, —CH$_2$—CH$_2$—, —CH=N, —N=N— and —N=N(O)—, $A^1$, $A^2$, $A^3$ and $A^4$ are identical or different divalent radicals, selected from the group consisting of 1,4-phenylene or 1,4-cyclohexylene radicals, substituted arylenes having 6 to 18 carbon atoms, substituted cycloalkylenes having 6 to 18 carbon atoms and heteroarylene having 4 to 10 carbon atoms, Z is identical or different di- to tetravalent benzene, 1,4-cyclohexane or 1,3-cyclopentane radicals, $A^5$ is identical or different, saturated or olefinically unsaturated alkyl, alkoxy or cycloalkyl radicals, having 1 to 16 carbon atoms, steroid radicals, halogen atoms, hydrogen atoms, hydroxyl, nitrile and trialkylsiloxy groups, having alkyl radicals which have 1 to 8 carbon atoms, a, b, c, d, f, g, h, and i independently of one another are identical or different integers having a value of 0, 1, 2 or 3, and sum of a+b+c+d+e+f+g+h+i is at least 2 and the sum of d and i is not more than 4, and e is a number having the value 0 or 1.

4. The process as claimed in claim 1, wherein the alkene and/or alkyne containing at least one methacryloxy or acryloxy group and mesogenic groups in the second step is one of the formula

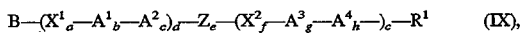

in which

B is a monovalent hydrocarbon radical of the formula $C_nH_m$ which is optionally substituted by halogen atoms and in which one or more non-adjacent methylene units can be replaced by oxygen atoms, n is an integer having a value from 2 to 20, m is an integer having the value (2n−1) or (2n−3), $X^1$ and $X^2$ are identical or different divalent radicals from the group consisting of —O—, —COO—, —CONH—, —CO—, —S—, —C≡C—, —CH=CH—, —CH$_2$—CH$_2$—, —CH=N, —N=N— and N=N(O)—, $A^1$, $A^2$, $A^3$ and $A^4$ are identical or different divalent radicals, selected from the group consisting of 1,4-phenylene or 1,4-cyclohexylene radicals, substituted arylenes having 6 to 18 carbon atoms, substituted cycloalkylenes having 6 to 18 carbon atoms and heteroarylene having 4 to 18 carbon atoms, Z is identical or different di- to tetravalent benzene, 1,4-cyclohexane or 1,3-cyclopentane radicals, $A^5$ identical or different, saturated or olefinically unsaturated alkyl, alkoxy or cycloalkyl radicals, having 1 to 16 carbon atoms, steroid radicals, halogen atoms, hydrogen atoms, hydroxyl, nitrile and trialkylsiloxy groups, having alkyl radials which have 1 to 8 carbon atoms, a, b, c, d, f, g, h, and i independently of one another are identical or different integers having a value of 0, 1, 2 or 3, and sum of a+b+c+d+e+f+g+h+i is at least 2 and the sum of d and i is not more than 4, and e is a number having the value 0 or 1, and $R^1$ is a radical of the formula

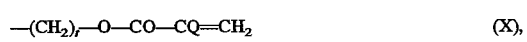

in which

Q is a methyl group or a hydrogen atom and t is an integer having a value from 0 to 10, and one or more non-adjacent methylene units can be replaced by oxygen atoms.

5. A liquid-crystalline polyorganosiloxane containing methacryloxy and/or acryloxy groups, which are prepared by the process as claimed in claim 1.

6. A process for crossing a liquid-crystalline polyorganosiloxane as claimed in claim 5 by UV light in the presence of photoinitiators and/or photosensitizers.

7. A three-dimensionally crosslinked liquid-crystalline polyorganosiloxane which is prepared by the process as claimed in claim 6.

* * * * *